United States Patent
Barth et al.

(10) Patent No.: US 6,793,826 B1
(45) Date of Patent: Sep. 21, 2004

(54) METHOD FOR RECOVERING INSOLUBLE SOLIDS FROM A MIXTURE

(75) Inventors: Charles Barth, Lawrence, MA (US); David Currit, Prosser, WA (US); Richard M. Western, Westford, MA (US)

(73) Assignee: Welch Foods, Inc., Concord, MA (US)

( * ) Notice: Subject to any disclaimer, the term of this patent is extended or adjusted under 35 U.S.C. 154(b) by 34 days.

(21) Appl. No.: 09/797,045

(22) Filed: Mar. 1, 2001

Related U.S. Application Data

(60) Provisional application No. 60/186,128, filed on Mar. 1, 2000.

(51) Int. Cl.[7] .............................................. B01D 21/32
(52) U.S. Cl. ...................... 210/739; 210/740; 210/745; 210/746; 210/803; 210/85; 210/92; 210/96.1; 426/495; 426/599; 99/277.1; 73/32 R; 73/53.01; 73/61.41; 73/61.71; 73/64.56
(58) Field of Search ............................. 426/495, 330.3, 426/330.4, 330.5, 599; 99/277, 277.1; 210/739, 803, 85, 92, 96.1, 740, 745, 746; 73/32 R, 53.01, 61.41, 61.71, 64.56

(56) References Cited

U.S. PATENT DOCUMENTS

| | | | | | |
|---|---|---|---|---|---|
| 2,806,217 | A | * | 9/1957 | Schmatz | 210/92 |
| 4,798,131 | A | * | 1/1989 | Ohta et al. | 99/277.2 |
| 4,819,552 | A | * | 4/1989 | Tazawa et al. | 99/277.2 |
| 4,889,743 | A | * | 12/1989 | Tazawa et al. | 99/277.2 |
| 4,891,236 | A | * | 1/1990 | Ohta et al. | 99/277 |
| 5,200,095 | A | * | 4/1993 | Franco et al. | 210/781 |

\* cited by examiner

*Primary Examiner*—Robert Popovics
(74) *Attorney, Agent, or Firm*—Bromberg & Sunstein LLP

(57) ABSTRACT

Methods for recovery of tartrate-containing, insoluble solids from an essentially settled grape-based mixture. More generally, methods for the recovery of insoluble solids, that have a predetermined characteristic from essentially settled mixtures are disclosed. The methods include performing proxy analyses on samples taken from the mixtures in order to determine at what time recovery should begin and end. Performing titration is detailed as a particular proxy analysis.

13 Claims, 3 Drawing Sheets

METHOD FOR RECOVERING INSOLUBLE SOLIDS FROM A MIXTURE

RELATED U. S. APPLICATION(S)

The present application claims priority from U.S. provisional application, Serial No. 60/186,128, filed Mar. 1, 2000, which is hereby incorporated herein by reference.

TECHNICAL FIELD

The present invention relates to recovery of insoluble solids from a liquid mixture. As a particular example, the invention relates to methods for the selective recovery of valuable tartrate-containing solid material that settles, over time, to the bottom of a container of pressed grape juice or wine.

BACKGROUND ART

Techniques to separate and harvest valuable subcomponents from liquid and from liquid-solid mixtures that contain varying proportions of soluble and insoluble solids have been under continuous development over many years. Methods for the clarification of these types of mixtures via natural sedimentation and separation of constituents without requiring agitation, centrifugation, or other application of force are appealing. However, practical problems to economically perform such separation of potentially valuable constituents from essentially worthless by-products remain.

For example, pressed fruit juices such as grape juice and other grape-based materials are typically, and undesirably, turbid or cloudy when first pressed. Such solid-liquid mixtures may be stored in tanks or other containers for long time periods so that they may settle for clarification and other purposes. A typical type of storage/settling tank, as is later described in detail, is fitted with a number of valved access ports located at different elevations. These access ports may be used to periodically draw samples for analyses. For example, samples may be drawn from the valved access ports on a weekly basis and analyzed to determine specific characteristics or properties present in the mixture at the corresponding levels within the tank. As mixture density will generally decrease with elevation, samples harvested from higher elevation ports will usually meet an accepted clarification level in a shorter storage time than the liquid that is closer to the bottom of the tank. As the mixture settles/clarifies over time, it may be drawn, as saleable product, from the tank via the upper valved access ports. Periodic analyses may eventually show no change in the measured characteristic (say, for example, volume percentage of insoluble solids or "ISS") at a particular level within the tank. At that time, that portion of the material below that level down to the bottom of the tank would be declared to be a "bottom." The term "tank bottom" is, therefore, used to describe the mixture of juice/liquid and sediment existing at or near the bottom of a tank of settled liquid or juice. Tank bottoms are not suitable for the production of finished products due to the high proportion of mixture components that have settled by gravity to the bottom of the tank or storage container.

"Filter trim" is generated as a resultant by-product during the process of recovering saleable/clarified grape juice from tank bottoms. Filter trim describes the solid material that is separated out of the mixture or "tank bottom." This is typically generated as a result of filtration, wherein diatomaceous earth (DE) may serve as a filtration aid. The DE is added to the liquid "tank bottoms" immediately prior to filtration and remains present in the "filter trim" in varying proportions depending on when, during the recovery process, the material is collected. Whether the "filter trim" is produced from single strength juice (herein denoted SS Bottoms) or comes from the processing of concentrate, it contains a significant amount of valuable tartrate precipitates. Excess argol (argol is, chemically, potassium bitartrate) separates from grape juice and wine precipitating in the form of crystals that gravitate to the bottom of the storage tank. These crystals are valuable as precursors for the production of cream of tartar, tartaric acid and other chemicals. This phenomenon is well known and was described, for example, in Reissued U.S. Pat. No. 14,636 to Welch, reissue date of Apr. 15, 1919. Screening and centrifugation techniques are therein described as typical argol recovery techniques. SS Bottoms are very inhomogeneous. Other insoluble solids, including bits of grape pulp and skin that remained after the pressing process, also may gravitate to the bottom of the storage tank. In this state, the aggregated, settled "tank bottom" material is not suitable for bottling and sale. The juice contained in the "Stank bottoms" should be recovered for use in the production of finished products; the "filter trim" portion should also be recovered with the DE and insoluble plant material effectively separated from the valuable argol.

Referring now to FIG. 1, tank 10 has valved access ports 11–15 with associated valves 111–115. Following settling/clarification, clarified juice, or other saleable liquids, may be drawn out of the tank at levels above the "tank bottom," shown as 100. Such drawing might occur by, per FIG. 1, siphoning out liquid through access port 13. Then, an operator desiring to clean out tank 10, filter the tank bottom 100, recover the juice therein and, thereby, also collect filter trim connects a pump 17 directly to a gutter valve 116 associated with gutter port 16 located at the bottom of storage tank 10. Activating pump 17 leads to a single step recovery of an entire tank bottom 100. Diatomaceous earth is added at unit 18 along fluid path, F. The juice separated at unit 19 is recovered along fluid path 192. The resulting solids (filter trim) separated at unit 19 are recovered along solids path 191. For single strength grape juice processing, for example, the consistency of SS Bottoms is that of a thick, free-flowing liquid that may contain anywhere from about 1% to about 15%, or more, insoluble solids (ISS). The ISS in SS Bottoms contains tartrates (also called argol) as well as a significant percentage of other insoluble plant material (particles of pulp, skin, etc.). Tartrates are crystalline and are heavier than the insoluble plant material. The non-homogeneous nature of SS Bottoms is such that the heavier ISS (tartrates) will tend to settle closer to the bottom of a tank 10 than the lighter ISS plant material. Using the above harvesting method via gutter port 16, suction caused by pump 17 inevitably creates a channel through the thickest/most dense material residing at the bottom of the tank 10. As a result, the lighter material near the top liquid surface may easily be pumped out through this channel and down fluid path F before much of the heavier material residing at the bottom of the tank 10 is extracted. Therefore, at flow onset, relatively little of the heavier tartrate-containing material is harvested before it becomes diluted, both in density and in economic value. As a result, it is difficult to ascertain when the tartrate content of the filter trim is high enough to make the collection and sale of the filter trim economically desirable.

SUMMARY OF THE INVENTION

In accordance with an embodiment, a method for recovery of tartrate-containing, insoluble solids from an essentially settled grape-based mixture is provided. The mixture is housed in a container having a sidewall, a bottom, a vertical axis, a valved gutter port capable of providing access to container contents through the bottom, and a plurality of valved access ports capable of providing access to container contents through the sidewall. The access ports are disposed upon the sidewall at heights defined as distances from the bottom measured along the vertical axis. A siphoning port is chosen from among the plurality of valved access ports. A first pumping system is attached to the siphoning port. A siphoning port valve is opened to provide fluid communication between container contents resident essentially above a siphoning height and the first pumping system through the sidewall. The first pumping system is activated and a first container contents portion resident essentially above the siphoning height is extracted. A second pumping system is then attached to the valved gutter port, the second pumping system having a conduit permitting samples of an extracted second container contents portion to be analyzed outside of the container. A gutter port valve is opened to provide fluid communication between container contents and the second pumping system through the bottom. The second pumping system is activated and data is generated over time regarding the extracted second container contents portion being collected. It is ascertained when to begin recovery of the desired insoluble solids, when to begin recovery determined to be when data generated indicates that the extracted second container contents portion is, essentially, tartrate-containing material.

Choosing a siphoning port may further include sampling container contents extracted from specific access ports to generate sampling data; and analyzing the sampling data in order to designate one of the plurality of access ports as the siphoning port. Sampling may further comprise determining a volume percentage of insoluble solids as sampling data. Analyzing may further comprise comparing volume percentages of insoluble solids obtained from ports so as to select the siphoning port as the port from which extracted container contents equals a lowest percentage, the lowest percentage defined to be a lowest percentage in excess of a predetermined volume percentage of insoluble solids. The predetermined volume percentage of insoluble solids may, in an embodiment, be, approximately, one volume percent. Generation of data may be obtained by subjecting extracted second container contents to titration. Ascertaining when to begin recovery may be achieved when the extracted second container contents portion is, essentially, tartrate-containing material. This may occur when data generated from titration indicates no less than 2.0% citric acid by weight.

In another embodiment, a method for recovery of insoluble solids from an essentially settled mixture is provided. The solids have a predetermined characteristic. The mixture is housed in a container having a sidewall, a bottom, a vertical axis, a valved gutter port capable of providing access to container contents through the bottom, and a plurality of valved access ports capable of providing access to container contents through the sidewall. The access ports are disposed upon the sidewall at heights defined as distances from the bottom measured along the vertical axis, The method includes choosing a siphoning port from among the plurality of valved access ports. A first pumping system is attached to the siphoning port. A siphoning port valve is opened to provide fluid communication between container contents resident essentially above a siphoning height and the first pumping system through the sidewall. The first pumping system is activated. A first container contents portion resident essentially above the siphoning height is extracted. A second pumping system is attached to the valved gutter port. The second pumping system has a conduit permitting samples of an extracted second container contents portion to be analyzed outside of the container. A gutter port valve is opened to provide fluid communication between container contents and the second pumping system through the bottom. The second pumping system is activated. Data is generated over time regarding the extracted second container contents portion being collected, the data correlatable with the predetermined characteristic. When to begin recovery is ascertained and is, determined to be when data generated indicates that the extracted second container contents portion has the predetermined characteristic. The insoluble solids are then recovered.

In yet another embodiment, a method for recovery of tartrate-containing, insoluble solids from tank bottoms is provided. The tank bottoms are housed in a container having a valved port. A collection system is attached to the valved port. The collection system has a conduit permitting samples of tank bottoms to be analyzed and at least one receptacle capable of collecting recovered solids.The valved port is opened. A proxy analysis is performed on samples of tank bottoms retrieved from the conduit The data generated as part of the proxy analysis is known to be correlatable with tartrate content of the samples. When to begin tartrate recovery is ascertained based upon results obtained from the proxy analysis. Recovered tartrate-containing insoluble solids are directed to the at least one receptacle.

DESCRIPTION OF SPECIFIC EMBODIMENTS

Generally, a method for recovery of insoluble solids, having a particular characteristic or value, from an essentially settled mixture involves, in an embodiment, at least two, steps. First, lighter material must be removed. In the case of mixtures resident in tanks or other containers, the lighter material naturally resident at greater distance or height from the tank bottom should be siphoned away. For mixtures stored in tank 10, one of the valved access ports 11–15 may be conveniently opened. Liquid resident essentially above the siphoning height is then removed and does not participate in the recovery process of the ISS material resident below Criteria must be established to decide which port to use for siphoning. Such criteria will vary depending upon the relative worth of the various mixture components, port availability, and mixture quantity. Sampling data may be generated from container contents. Such data is analyzed to determine which material may most valuably be siphoned away. Herein and in the appended claims, grape-based mixtures or products grape-based materials refer to all solid, semi-solid, liquid, and solid-liquid mixtures including, but not limited to juices, concentrates, drinks, and wine. In the case of grape-based mixtures (with argol crystals being the desired recovery target), the volume percentage of ISS defines a suitable criterion. A common method of determining ISS is spin centrifugation, wherein a small sample (typically, about 50 ml) is placed into a graduated test tube.

The test tube is then positioned in a centrifuge and spun such that, because of the centrifuge design, essentially all insoluble material accumulates at the bottom of the tube. The ISS volume percentage may conveniently be determined from the graduations.

Figure 1:
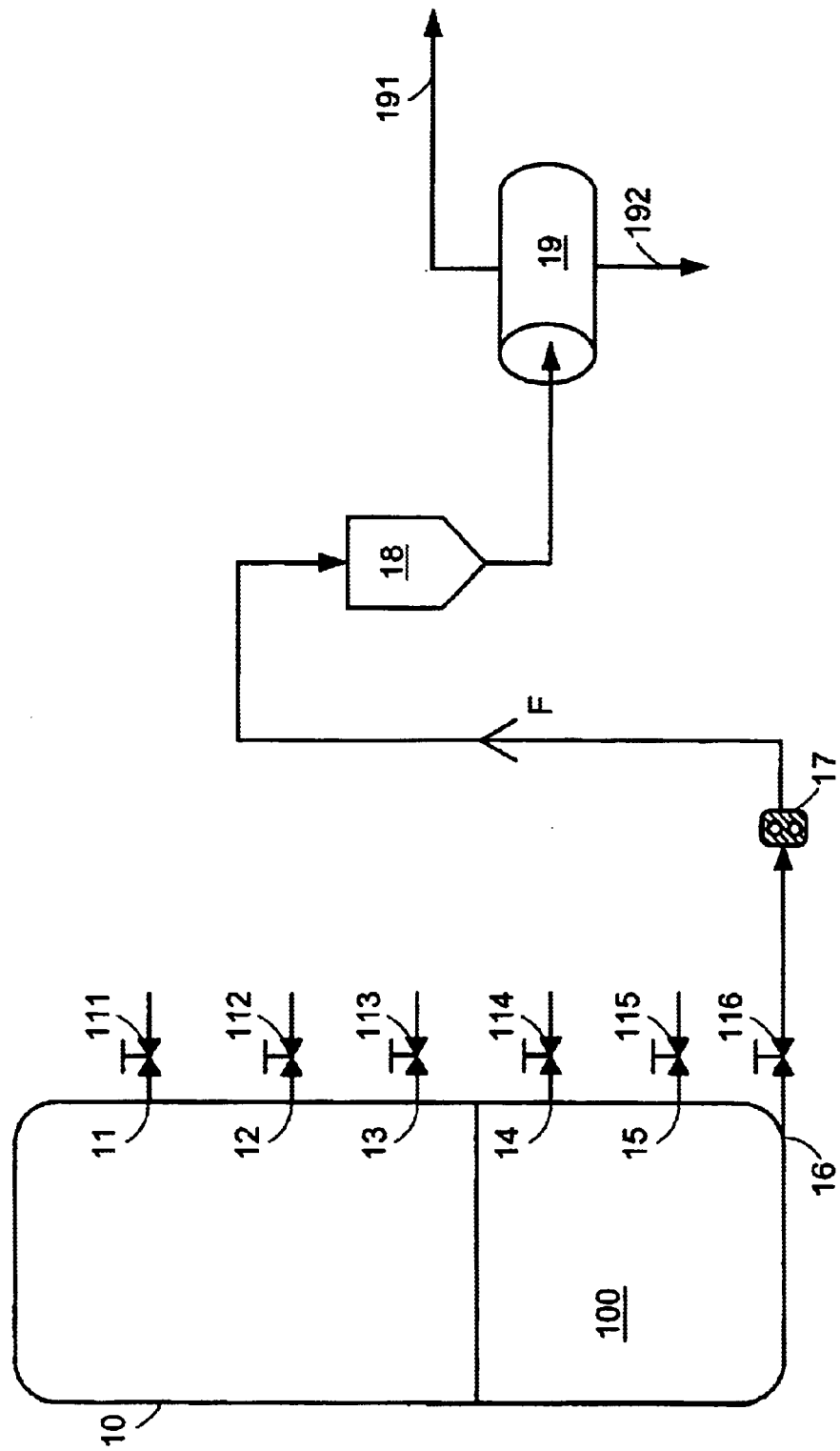
FIG. 1 is a schematic representation of a prior art method for recovering insoluble solids from a tank bottom.
Figure 2:
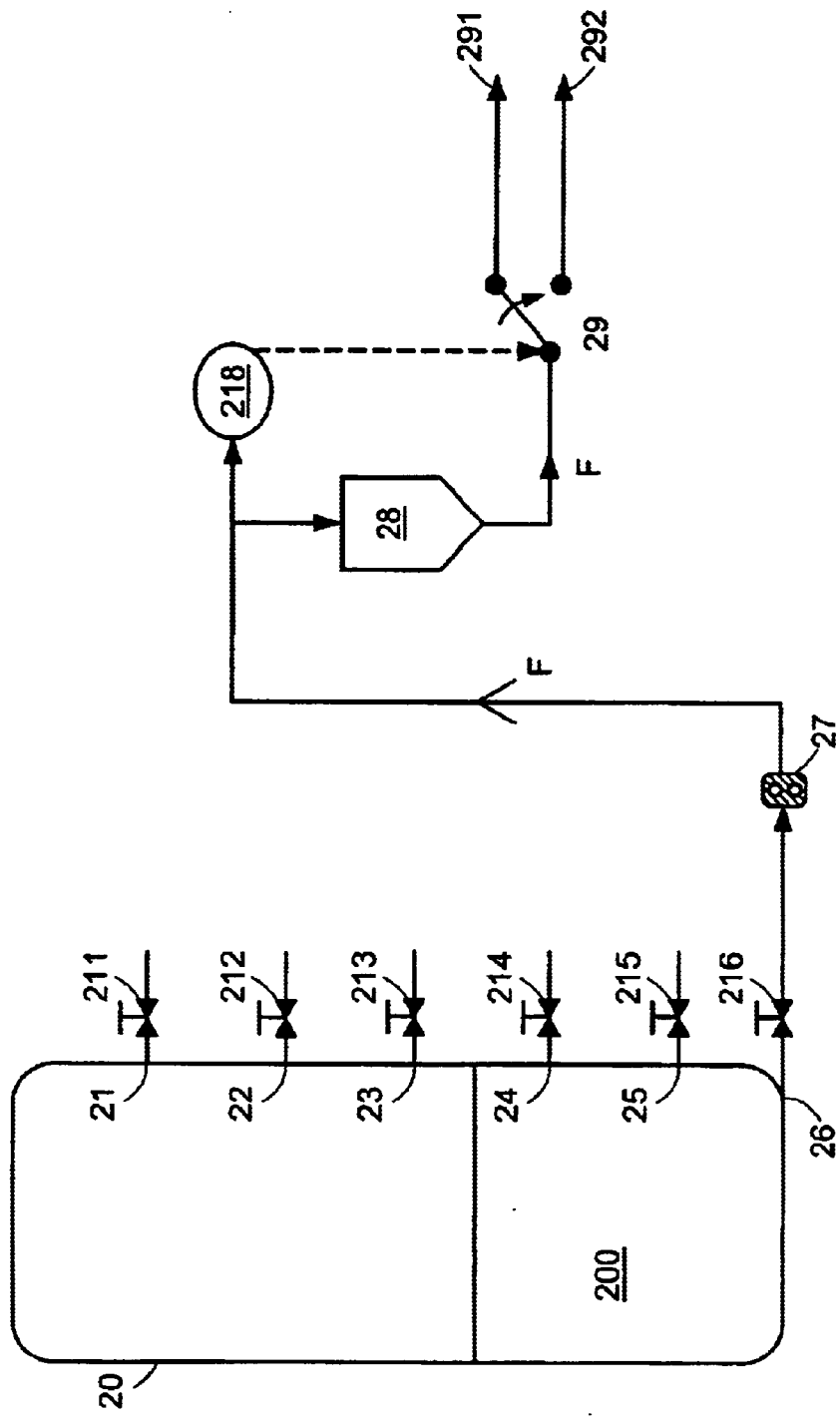
FIG. 2 is a schematic representation of a method for recovering specific insoluble solids based upon proxy analysis according to an embodiment of the invention.

Referring now to FIG. 2, the ISS of samples of contents of tank 20 taken in turn, from the available access ports 21–25 (when associated valves 211–215 are, in turn, opened) are measured. As an example, a sample may be taken from port 23 and is measured to have somewhat more than one percent by volume ISS. A sample from port 22 is measured to have somewhat less than one percent. A reasonable choice for the siphoning port would be port 23 because, particularly in the case of tartrates from grape juice, the value of what might be harvested from tank bottom material 200 having less than one percent ISS drops sharply. Siphoning may be accomplished by any practical method of liquid transfer, such as gravity, pumping, or forcing (by increasing the hydrostatic pressure inside the tank) with the use of a compressor or external pump (not shown). In a particular embodiment, pump 27 might be attached to port 23, valve 213 would be opened, and, with activation of pump 27, mixture contents resident essentially at heights greater than the height of port 23 would be siphoned off. Pump 27 may then be disconnected from port 23. Pump 27 may be subsequently used in conjunction with the second step of insoluble solid recovery, in accordance with particular embodiments. In FIG. 2, pump 27 is shown in such manner.

After the lighter material has been siphoned off, the second step of the process is to recover only that portion of the usually heavier, insoluble material that contains a substantial proportion of the desired material. The desired portion may neither have an easily discernible characteristic nor an apparent means for its separation from the undesirable portion. In an embodiment, a proxy analysis is effectively performed. Most generally, a quantifiable property of the mixture is found, by experimentation, to be correlatable with another known property of the desired material. A proxy analysis, herein defined in this specification and appended claims, is one, which, consists of tests aimed at measuring this quantifiable property and alerting when to begin and end the recovery of the desired material. Such proxy analysis may be applicable to the separation and collection of solid or liquid sub-components from either liquids, solids, or liquid-solid mixtures. Most generically, one or more simple analyses (such as, but not limited to, acid, color, turbidity, conductivity, solubility, density) serve as an easier proxy for more difficult and potentially time-consuming experimentation. In this way, one could potentially identify a correlation between the analyses of the desired, valuable material and one (or more) of the other, simpler analyses. The valuable material could then be recovered on the basis of the proxy analysis for some other property or material that was quicker and/or easier to perform. The actual specific analyses would need to be determined by, and based upon specific experimentation with the actual materials to be separated and recovered.

A proxy analysis found, by experimentation, to give an effective indication of when to begin and end collection of tartrates from grape-based product so as to avoid collecting quantities of undesirable material is online titration. An example of a titration procedure is outlined in Example 1.

EXAMPLE 1

Titration Procedure

Reagents and Apparatus

1. Distilled water
2. 0.1 N Sodium Hydroxide solution
3. pH 7.00 buffer
4. pH meter with an Ag/AgCl internal electrode and a calomel reference electrode
5. Ring stand and clamps
6. Tygon tubing
7. 50 mL titrating burette
8. Glass or nalgene aspirator bottle (20 liter) with spigot
9. Magnetic stirrer plate and magnetic stirring bar
10. 10 mL and 24 mL volumetric pipettes
11. 250 mL and 400 mL beakers
12. Mettler balance
13. Waring blender
14. Hot plate or burner Procedure 1. Measure the aliquot of sample into a 250 mL beaker.
2. Add about 100 mL distilled water to the beaker.
3. Standardize the pH meter with 7.00 buffer solution.
4. Place beaker of sample material (and containing stirring bar) onto the magnetic stirrer plate. Adjust to a medium motor speed that will provide good agitation, but not so fast as to cause stirring bar to bounce against the beaker or electrodes.
5. Insert the electrodes far enough into the beaker so that the bulb portion of the glass electrode is completely immersed in the sample, but not so far as to interfere with rotation of the stirring bar.

NOTE: Be sure the electrodes do not touch the walls of the beaker.

6. Position the titrating burette over the sample beaker and turn the function switch of the pH meter to "pH."
7. With 0.1 N Sodium Hydroxide solution (NaOH), titrate rapidly to a scale reading on the meter of 7.00 pH. Next, introduce the NaOH slowly at a rate of 4 drops/addition to 8.00 pH. Then, add the solution a drop at a time to an 8.10 pH endpoint.

NOTE: The pH value of 8.10 is considered the equivalence point for the neutralization of organic acids in fruit products.

8. Read the graduated scale of the burette and record the number mL NaOH used in the titration.

Titration Calculation

The theoretical equivalent weight of Citric Acid is 0.064. Assume a 25 mL aliquot of sample was checked for acid and 11.4 mL of 0.1 N NaOH was used.

$$\frac{\text{mL NaOH} \times N \text{ NaOH} \times \text{factor} \times 100}{\text{Sample aliquot unit}} = \text{g}/100 \text{ mL as Citric}$$

$$\frac{11.4 \times 0.1 \times 0.064 \times 100}{25} = 0.29 \text{ g}/100 \text{ mL as Citric}$$

Figure 3:
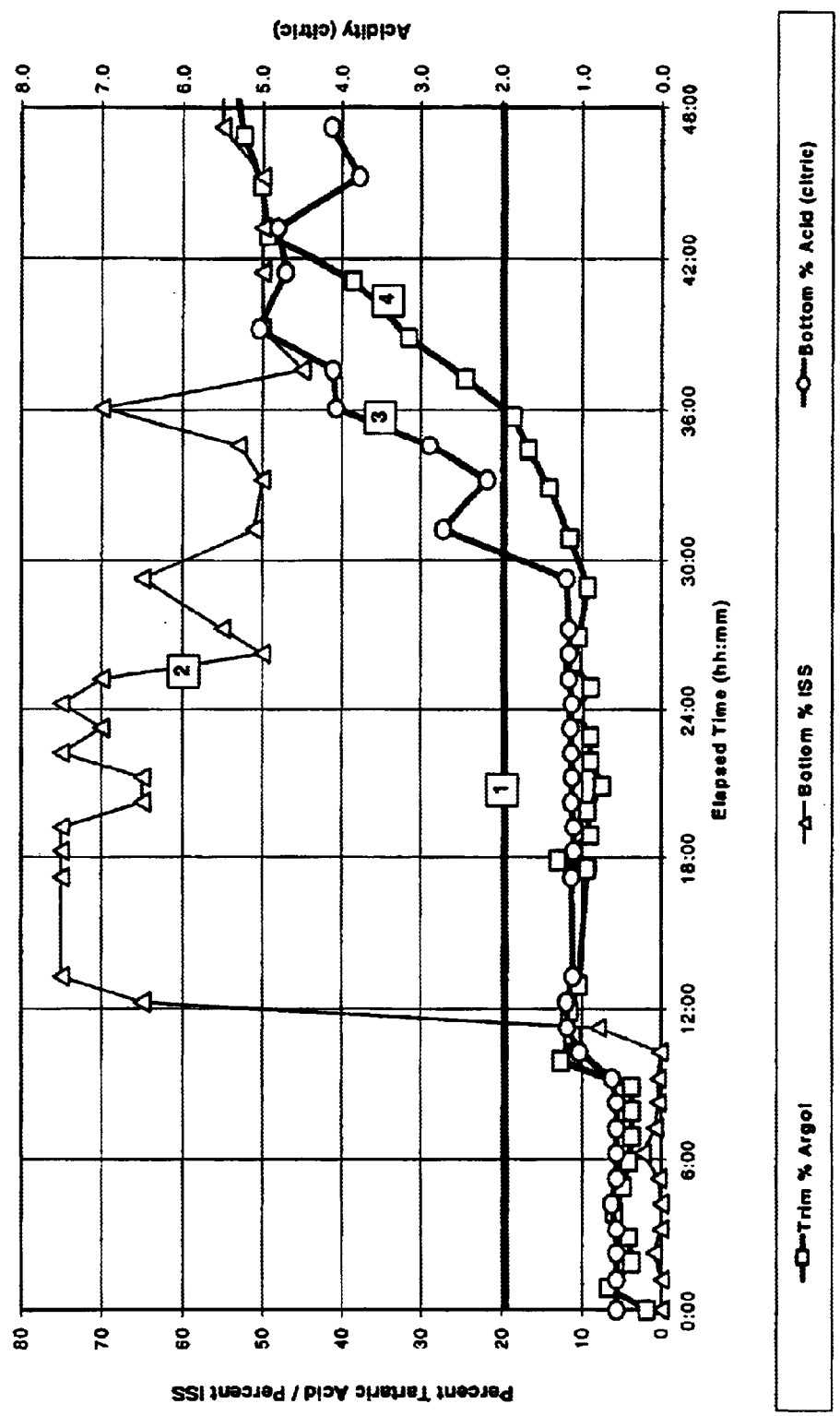
FIG. 3 is a chart plotting the experimental data associated with Example 1.

Associated with the titration procedure followed in Example 1, refer now to TABLE 1 The data of TABLE 1 illustrates that, in this specific embodiment, a titration analysis for wt % citric acid was found to be an appropriate proxy analysis for determining, online, the % Argol in filter trim. The data was collected periodically over the course of a tank bottom processing run. The first two columns in TABLE 1 show the % Argol in samples of the filter trim obtained periodically during the run. The last three columns show the % ISS and the % citric acid in samples of liquid tank bottoms material. This data tends to indicate that the % ISS is initially low, but increases sharply early in the course of the processing run. From this experimental data, it may be concluded, somewhat surprisingly, that % ISS is not correlated with the % Argol, while the % citric acid is correlated with the % Argol. The data is plotted in FIG. 3, also illustrating the experimental finding that the level of Argol in filter trim is correlated to the percent citric acid in the liquid tank bottoms material. Empirically, as indicated at line 1, a value of approximately two weight percent citric acid (curve 3) was found to be an effective lower cutoff value at which level (and above) tartrate content (curve 4) increased above 10%. It can also be seen, in FIG. 3, that the % ISS (curve 2) increases in a much shorter elapsed time than does the % Argol. The % ISS is, therefore, not correlatable with % Argol in the filter trim. Simply stated, curve 3 tracks with curve 4, whereas curve 2, somewhat unexpectedly, does not track with curve 4.

Therefore, referring back to FIG. 2, in an embodiment, samples are removed from the flow path F and sent to proxy analysis unit 218 (which for the tartrate recovery embodiment may be a titration unit as described). The remaining bulk of the tank bottom material 200 being pumped by pump 27 from gutter port 26 (with valve 216 open) along flow path F is converted into filter trim by the addition of diatomaceous earth at unit 28. A flow path decision is made at point 29, based on the proxy analysis (218). If the proxy analysis, in this case, the titration results, leads to a determination that less than approximately two weight percent citric acid is present in the sampled filter trim, the filter trim is to be sent to the waste flow path 291. If the titration yields a measure of at least approximately two weight percent citric acid, the filter trim is to be redirected to the collection flow path 292. Additional flow paths may also be defined for the purposes of further processing or lot segregation based on other factors (for example, varying % Argol levels), as determined via proxy analysis. Redirection of the flow, at decision point 29, or other location, may be accomplished either manually or, alternatively, automatically through utilization of automated or other process controls known in the art.

TABLE 1

| FILTER TRIM ANALYSES | | LIQUID BOTTOMS ANALYSES | | |
|---|---|---|---|---|
| Total Time | Trim % Argol | Total Time | Bottom % IS S | Bottom % Acid (citric) |
| 0:00 | 1.85 | 0:00 | 0.9 | 0.56 |
| 0:55 | 6.88 | 1:15 | 0.1 | 0.56 |
| 1:55 | 3.71 | 2:15 | 0.1 | 0.56 |
| 2:55 | 4.08 | 3:15 | 0.3 | 0.58 |
| 3:55 | 5.94 | 4:15 | 2.4 | 0.82 |
| 4:55 | 4.82 | 5:15 | 0.8 | 0.68 |
| 5:55 | 4.08 | 6:15 | 0.4 | 0.58 |
| 6:55 | 3.71 | 7:15 | 0.4 | 0.56 |
| 7:55 | 3.71 | 8:15 | 0.2 | 0.58 |
| 8:55 | 3.71 | 9:15 | 7.9 | 0.61 |
| 9:55 | 12.61 | 10:15 | 65 | 1.03 |
| 10:55 | 11.13 | 11:15 | 75 | 1.18 |
| 11:55 | 11.50 | 12:15 | 76 | 1.19 |
| 12:55 | 10.39 | 13:15 | 75 | 1.11 |
| 17:35 | 9.27 | 17:15 | 75 | 1.13 |
| 17:55 | 12.98 | 18:15 | 65 | 1.1 |
| 18:55 | 8.90 | 19:15 | 65 | 1.1 |
| 19:55 | 9.27 | 20:15 | 75 | 1.13 |
| 20:55 | 7.42 | 21:15 | 70 | 1.12 |
| 21:55 | 8.90 | 22:15 | 76 | 1.13 |
| 22:55 | 8.90 | 23:15 | 70 | 1.14 |
| 23:55 | 10.76 | 24:15 | 50 | 1.12 |
| 24:55 | 8.90 | 25:15 | 55 | 1.16 |
| 25:55 | 11.13 | 26:15 | 65 | 1.16 |
| 26:55 | 10.39 | 27:15 | 51 | 1.16 |
| 28:55 | 9.27 | 29:15 | 50 | 1.19 |
| 30:55 | 11.60 | 31:15 | 53 | 2.72 |
| 32:55 | 14.10 | 33:15 | 70 | 2.18 |
| 34:25 | 16.69 | 34:35 | 45 | 2.89 |
| 35:45 | 18.55 | 36:05 | 50 | 4.07 |
| 37:15 | 24.48 | 37:35 | 50 | 4.11 |
| 38:55 | 31.53 | 39:15 | 50 | 5.04 |
| 41:10 | 38.58 | 41:30 | 50 | 4.71 |
| 42:55 | 49.34 | 43:15 | 55 | 4.81 |
| 44:55 | 50.08 | 45:15 | 45 | 3.78 |
| 46:55 | 52.31 | 47:15 | 50 | 4.13 |
| 48:55 | 53.42 | | | |

Although the invention has been described with reference to a specific embodiment, it will be understood by one of ordinary skill in the art that various modifications can be made without departing from the spirit and the scope of the present invention.

We claim:

1. A method for recovery of tartrate-containing, insoluble solids from an essentially settled grape-based mixture, the mixture housed in a container, the container having a sidewall, a bottom, a vertical axis, a valved gutter port capable of providing access to container contents through the bottom, and a plurality of valved access ports capable of providing access to container contents through the sidewall, the access ports disposed upon the sidewall at heights defined as distances from the bottom measured along the vertical axis, the method comprising:

choosing a siphoning port from among the plurality of valved access ports;

attaching a first pumping system to the siphoning port;

opening a siphoning port valve to provide fluid communication between container contents resident essentially above a siphoning height and the first pumping system through the sidewall;

activating the first pumping system;

extracting a first container contents portion resident essentially above the siphoning height;

attaching a second pumping system to the valved gutter port, the second pumping system comprising:
 a conduit permitting samples of an extracted second container contents portion to be analyzed outside of the container;

opening a gutter port valve to provide fluid communication between container contents and the second pumping system through the bottom;

activating the second pumping system;

generating data over time regarding the extracted second container contents portion being collected;

ascertaining when to begin recovery, when to begin recovery determined to be when data generated indicates that the extracted second container contents portion is, essentially, tartrate-containing material; and recovering tartrate-containing insoluble solids.

2. A method according to claim 1 wherein choosing further comprises:

sampling, container contents extracted from specific access ports to generate sampling data; and analyzing the sampling data in order to designate one of the plurality of access ports as the siphoning port.

3. A method according to claim 2 wherein sampling further comprises determining a volume percentage of insoluble solids as sampling data; and wherein analyzing further comprises comparing volume percentages of insoluble solids obtained from ports so as to select the siphoning port as the port from which extracted container contents equals a lowest percentage, the lowest percentage defined to be a lowest percentage in excess of a predetermined volume percentage of insoluble solids.

4. A method according to claim 3 wherein the predetermined volume percentage of insoluble solids is approximately one volume percent.

5. A method according to claim 1 wherein, in generating, data is obtained by subjecting extracted second container contents to titration.

6. A method according to claim 5 wherein, in ascertaining, extracted second container contents portion is, essentially, tartrate-containing material when data generated from titration indicates no less than approximately 2.0% citric acid by weight.

7. A method according to claim 1 wherein, after extracting, the first pumping system is detached from the siphoning port and, acting as a second pumping system, is, in attaching, attached to the valved gutter port.

8. A method for recovery of insoluble solids from an essentially settled mixture, the solids having a predetermined percentage of insoluble solids, the mixture housed in a container, the container having a sidewall, a bottom, a vertical axis, a valved gutter port capable of providing access to container contents through the bottom, and a plurality of valved access ports capable of providing access to container contents through the sidewall, the access ports disposed upon the sidewall at heights defined as distances from the bottom measured along the vertical axis, the method comprising:

choosing a siphoning port from among the plurality of valved access ports;

attaching a first pumping system to the siphoning port; opening a siphoning port valve to provide fluid communication between container contents resident essentially above a siphoning height and the first pumping system through the sidewall;

activating the first pumping system;

extracting a first container contents portion resident essentially above the siphoning height;

attaching a second pumping system to the valved gutter port, the second pumping system comprising:

a conduit permitting samples of an extracted second container contents portion to be analyzed outside of the container;

opening a gutter port valve to provide fluid communication between container contents and the second pumping system through the bottom;

activating the second pumping system;

generating data over time regarding the extracted second container contents portion being collected, the data correlatable with the predetermined percentage of insoluble solids;

ascertaining when to begin recovery, when to begin recovery determined to be when data generated indicates that the extracted second container contents portion has the predetermined percentage of insoluble solids; and recovering the insoluble solids.

9. A method according to claim 8 wherein choosing further comprises:

sampling container contents extracted from specific access ports to generate sampling data; and analyzing the sampling data in order to designate one of the plurality of access ports as the siphoning port.

10. A method according to claim 9 wherein sampling further comprises determining a volume percentage of insoluble solids as sampling data; and wherein analyzing further comprises comparing volume percentages of insoluble solids obtained from ports so as to select the siphoning port as the port from which extracted container contents equals a lowest percentage, the lowest percentage defined to be a lowest percentage in excess of a predetermined volume percentage of insoluble solids.

11. A method according to claim 10 wherein the predetermined volume percentage of insoluble solids is approximately one volume percent.

12. A method according to claim 8 wherein, after extracting, the first pumping system is detached from the siphoning port and, acting as a second pumping system, is, in attaching, attached to the valved gutter port.

13. A method for recovery of tartrate-containing, insoluble solids from tank bottoms, the tank bottoms housed in a container having a valved port, the method comprising:

attaching a collection system to the valved port, the collection system comprising:

a conduit permitting samples of tank bottoms to be analyzed; and at least one receptacle capable of collecting recovered solids;

opening the valved port; performing a proxy analysis on the samples of tank bottoms retrieved from the conduit, data generated known correlatable with tartrate content of the samples;

ascertaining when to begin recovery based upon results obtained from the proxy analysis; and directing recovered tartrate-containing insoluble solids to the at least one receptacle.

\* \* \* \* \*

UNITED STATES PATENT AND TRADEMARK OFFICE
CERTIFICATE OF CORRECTION

PATENT NO.   : 6,793,826 B1                                                     Page 1 of 1
DATED        : September 21, 2004
INVENTOR(S)  : Charles Barth et al.

It is certified that error appears in the above-identified patent and that said Letters Patent is hereby corrected as shown below:

Column 9,
Line 8, replace "sampling," with -- sampling --.

Signed and Sealed this

First Day of February, 2005

JON W. DUDAS
*Director of the United States Patent and Trademark Office*